(12) United States Patent
Park et al.

(10) Patent No.: US 12,165,313 B2
(45) Date of Patent: Dec. 10, 2024

(54) DEEP LEARNING ARCHITECTURE SYSTEM FOR AUTOMATIC FUNDUS IMAGE READING AND AUTOMATIC FUNDUS IMAGE READING METHOD USING DEEP LEARNING ARCHITECTURE SYSTEM

(71) Applicant: ARK Inc., Busan (KR)

(72) Inventors: Keun Heung Park, Busan (KR); Han jo Kwon, Busan (KR)

(73) Assignee: ARK INC., Busan (KR)

(*) Notice: Subject to any disclaimer, the term of this patent is extended or adjusted under 35 U.S.C. 154(b) by 819 days.

(21) Appl. No.: 17/423,016

(22) PCT Filed: Nov. 27, 2019

(86) PCT No.: PCT/KR2019/016422
§ 371 (c)(1),
(2) Date: Jan. 10, 2022

(87) PCT Pub. No.: WO2020/149518
PCT Pub. Date: Jul. 23, 2020

(65) Prior Publication Data
US 2022/0189012 A1    Jun. 16, 2022

(30) Foreign Application Priority Data

Jan. 14, 2019 (KR) .................. 10-2019-0004572
Nov. 4, 2019 (KR) .................. 10-2019-0139535

(51) Int. Cl.
*G06T 7/00* (2017.01)
*A61B 3/00* (2006.01)
(Continued)

(52) U.S. Cl.
CPC .......... *G06T 7/0012* (2013.01); *A61B 3/0025* (2013.01); *A61B 3/12* (2013.01);
(Continued)

(58) Field of Classification Search
CPC ........... G06T 7/001; G06T 2207/20081; G06T 2207/20084; G06T 2207/30041;
(Continued)

(56) References Cited

U.S. PATENT DOCUMENTS 10,896,354 B2 * 1/2021 Yang .................. G06N 3/045
11,941,809 B1 * 3/2024 Bhuiyan .............. G16H 50/30
(Continued)

FOREIGN PATENT DOCUMENTS

| KR | 10-1810289 B1 | 12/2017 |
| KR | 10-2018-0021635 A | 3/2018 |
| WO | WO 2018/035473 A2 | 2/2018 |

OTHER PUBLICATIONS

International Search Report for PCT/KR2019/016422 mailed Mar. 2, 2020 from Korean Intellectual Property Office.

*Primary Examiner* — Lewis G West
(74) *Attorney, Agent, or Firm* — Paratus Law Group, PLLC

(57) ABSTRACT

Disclosed are an algorithm for automatic fundus image reading, and a deep learning architecture for automatic fundus image reading, which are capable of minimizing the amount of data required for learning by training and reading artificial intelligence in a manner similar to that of an ophthalmologist who acquires medical knowledge.

11 Claims, 4 Drawing Sheets

(51) Int. Cl.
- *A61B 3/12* (2006.01)
- *G06V 10/40* (2022.01)
- *G06V 10/764* (2022.01)
- *G06V 10/774* (2022.01)
- *G06V 10/776* (2022.01)
- *G06V 10/82* (2022.01)
- *G06V 10/98* (2022.01)
- *G16H 30/40* (2018.01)
- *G16H 50/20* (2018.01)

(52) U.S. Cl.
CPC ............ *G06V 10/40* (2022.01); *G06V 10/764* (2022.01); *G06V 10/774* (2022.01); *G06V 10/776* (2022.01); *G06V 10/82* (2022.01); *G06V 10/993* (2022.01); *G16H 30/40* (2018.01); *G16H 50/20* (2018.01); *G06T 2207/20081* (2013.01); *G06T 2207/20084* (2013.01); *G06T 2207/30041* (2013.01); *G06T 2207/30096* (2013.01); *G06T 2207/30168* (2013.01); *G06V 2201/03* (2022.01)

(58) Field of Classification Search
CPC . G06T 2207/30096; G06T 2207/30168; G06T 7/0002; A61B 3/0025; A61B 3/12; A61B 3/113; A61B 3/14; A61B 5/00; G06V 10/40; G06V 10/764; G06V 10/774; G06V 10/776; G06V 10/82; G06V 10/993; G06V 2201/03; G06V 20/698; G16H 30/40; G16H 50/20; G16H 50/70
See application file for complete search history.

(56) References Cited

U.S. PATENT DOCUMENTS

| | | | |
|---|---|---|---|
| 2018/0140180 A1* | 5/2018 | Coleman | G06T 7/0012 |
| 2018/0146912 A1 | 5/2018 | Rundo et al. | |
| 2018/0247405 A1 | 8/2018 | Kisilev et al. | |
| 2019/0220973 A1* | 7/2019 | Cho | G06T 7/136 |
| 2019/0221313 A1* | 7/2019 | Rim | G06F 18/217 |
| 2023/0192881 A1* | 6/2023 | Brooks | C07K 16/18 424/143.1 |
| 2024/0233947 A1* | 7/2024 | Kondo | G06V 10/764 |
| 2024/0257899 A1* | 8/2024 | Sato | G16B 40/00 |

* cited by examiner

DEEP LEARNING ARCHITECTURE SYSTEM FOR AUTOMATIC FUNDUS IMAGE READING AND AUTOMATIC FUNDUS IMAGE READING METHOD USING DEEP LEARNING ARCHITECTURE SYSTEM

CROSS-REFERENCE TO RELATED APPLICATIONS

This application is a National Stage Patent Application of PCT International Patent Application No. PCT/KR2019/016422 (filed on Nov. 27, 2019) under 35 U.S.C. § 371, which claims priority to Korean Patent Application Nos. 10-2019-0004572 (filed on Jan. 14, 2019) and 10-2019-0139535 (filed on Nov. 4, 2019), which are all hereby incorporated by reference in their entirety.

BACKGROUND

The present invention relates to an algorithm for automatic fundus image reading, and a deep learning architecture for automatic fundus image reading, which can minimize the amount of data required for learning by training and reading artificial intelligence in a manner similar to that of an ophthalmologist who acquires medical knowledge.

According to a paper on automatic reading of diabetic retinopathy published by Google in 2016, about 100,000 learning data generated by 50 or more doctors are used to determine one diabetic retinopathy. Although it shows a good result in the end, the disadvantage is that too much effort is required to train one disease. On the other hand, in the case of human, the amount of fundus pictures that a person learns until he or she becomes an ophthalmologist is much smaller than that of the learning data. Therefore, an algorithm like this has been devised based on the idea that the amount of required learning data can be greatly reduced when an artificial intelligence is configured in a manner similar to the method of reading by a human doctor.

When viewing and reading medical images, a human doctor intuitively and roughly looks at overall images and infers a broad disease category. After that, the human doctor enlarges and examines the images in detail and finds lesions essential for diagnosis of a disease described in medical textbooks to confirm the disease. Pondering on this process, it seems that the human doctor has one piece of knowledge that intuitively recognizes the overall outline and additionally has another knowledge system for separately recognizing individual lesions. That is, as the system is configured of a knowledge branch that sees the whole and a branch that sees lesions, it is determined that the amount of learning data may be reduced when the system is created as an algorithm and applied to artificial intelligence.

On the other hand, a deep learning neural network that has brought remarkable development in the field of image recognition recently is a convolutional neural network (CNN). The convolutional neural network is characterized in that a first input image data is repeatedly convoluted by a filter, and a result of the convolution is delivered to the layer of next stage. Starting from AlexNet in an early stage, convolutional neural network architectures include Google's LeNet, Inception, ResNet characterized by skip connection, and the like. Although these architectures are different from each other, commonly, they are configured of a feature extraction part for extracting global features while vertically accumulating convolutions, and a classification layer that makes a decision. The artificial neural network has a problem of obscuring the information on the front side as the layer goes deeper, instead of smoothly transferring the information to the back side. This is the same when backpropagation occurs in a learning process, and as an error is scarcely transferred while going back to the front side and thus learning is not performed well in the backpropagation process of the error, the weight values of the neural network are hardly updated. The problem that the layers on the front side are not trained well in the backpropagation process of the error is also called as a vanishing gradient problem.

Therefore, an object of the present invention is to provide a deep learning architecture system for automatic fundus image reading, which can solve this problem, carry out learning with a small amount of data, and automatically read fundus images using features of the fundus images among medical images, through a method of rapidly training only a relatively small number of bottlenecks without training the entire neural network from the scratch, by rather inversely taking advantage of these features of the artificial neural network.

SUMMARY

Therefore, the present invention has been made in view of the above problems, and it is an object of the present invention to provide an algorithm capable of minimizing the amount of data required for learning fundus images and automatically reading the fundus images by training artificial intelligence in a way similar to that of an ophthalmologist who acquires medical knowledge.

The technical problems to be solved by the present invention are not limited to the technical problems mentioned above, and unmentioned other technical problems will be clearly understood by those skilled in the art from the following description.

To accomplish the above object, according to one aspect of the present invention, there is provided a deep learning architecture system for automatic fundus image reading, the system comprising: a trunk module 100 that combines common parts in a plurality of convolutional neural network (CNN) architectures into one part, the CNN architecture having one or more serially arranged feature extraction layer sets respectively configured of a plurality of convolutional layers for performing feature extraction on a fundus image and one pooling layer for performing subsampling to reduce the amount of computation;
  a plurality of branch modules 200 for receiving an output of the trunk module 100 that has generated an architecture for each of the branch modules 200, identifying a lesion from the fundus image, and diagnosing a corresponding disease name;
  a section 110 which is an architecture that connects any one branch module 200 among the plurality of branch modules 200 to the trunk module 100;
  a root layer 120 for connecting the trunk module 100 and the branch module 200 by transferring an output of a specific layer of the trunk module 100 to the branch module 200; and
  a final diagnosis unit 300 for integrating diagnosis data received from the plurality of branch modules 200 to determine and output a final disease name.

Through the means of solving the problems, the present invention may provide an algorithm capable of effectively and automatically reading fundus images by minimizing the amount of data required for learning the fundus images.

In addition, the present invention may provide an algorithm capable of reflecting the classification system of medical terms through mixed classification according to class.

In addition, the present invention may provide a detector finely tuned to fit a lesion of a small size to easily identify a lesion from a fundus image.

In addition, the present invention has an effect of only partially training a system as needed without affecting the entire system while individually training each branch module.

In addition, since common parts are reduced, the present invention may simultaneously decrease the amount of calculation and storage required for computing.

In addition, the present invention may use architectures that perform different functions, such as a classifier branch for classifying the category of fundus images and an object detector branch for finding a specific lesion of interest from a fundus image, as one architecture, while taking advantage of the architectures.

In addition, when there occurs a certain change and the neural network needs to be retrained, the present invention may train only a branch that needs to be retrained, rather than retraining the entire neural network.

In addition, the present invention is efficient in that as only a diagnosis name is separately labeled as needed and only a lesion is labeled as needed when a training set of [image+label] is prepared to train a neural network, labels may be configured separately for each branch.

In addition, the present invention is efficient in that the entire architecture is not used to use a specific function since only a section may be separated to separately use only a function thereof when only an individual function is needed among the functions of the entire neural network.

In addition, the present invention is easy to add a new function since when a new label list and labeled data are prepared after a neural network is already trained, a new function may be created in the neural network by adding only one more branch to process.

In addition, the present invention has an effect of processing fast compared to independently executing individual architectures.

DETAILED DESCRIPTION

Figure 1:
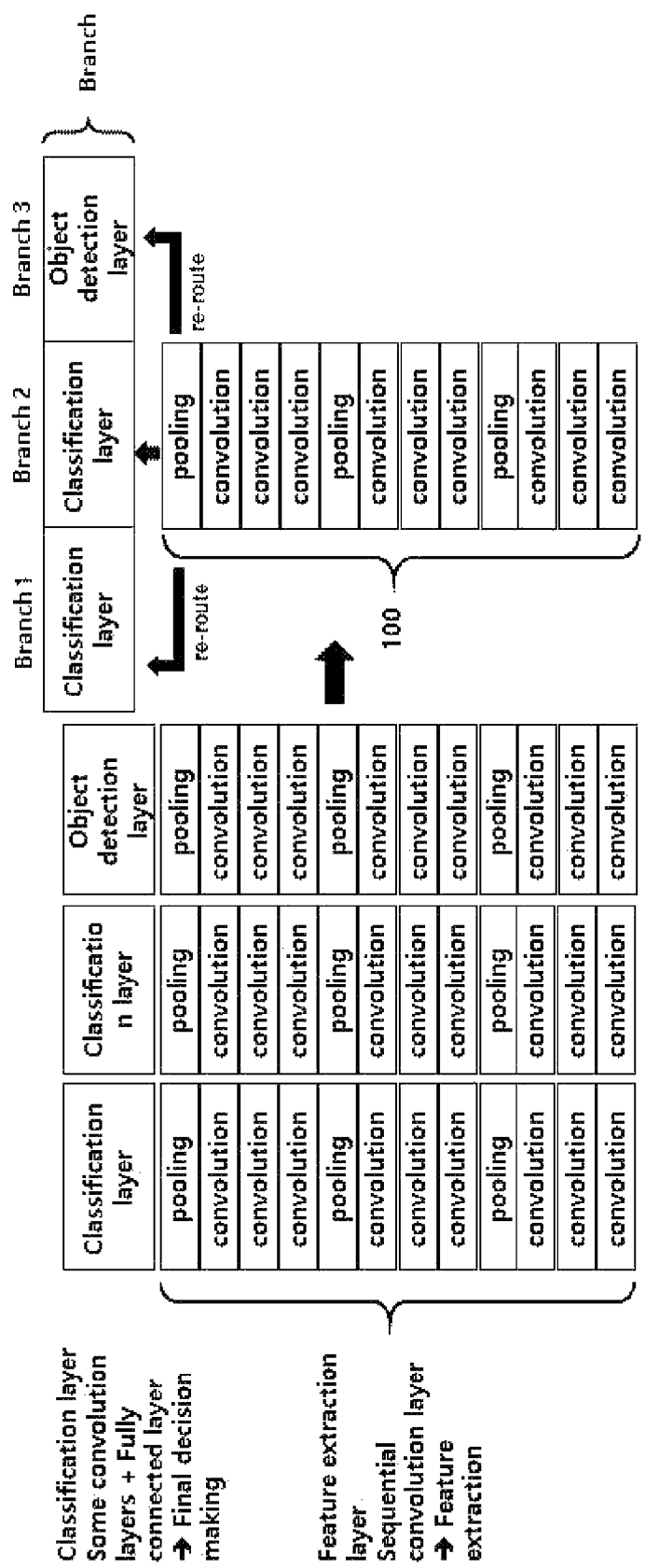
FIG. 1 is a view showing the configuration of a deep learning architecture system for automatically reading medical images, showing HydraNet, the basic architecture of the present invention.

The terms used in this specification will be briefly described, and the present invention will be described in detail.

Although general terms widely used at present are selected as the terms used in this specification as much as possible considering the functions of the present invention, this may vary according to the intention of those skilled in the art, precedents, or emergence of new techniques. Therefore, the terms used in the present invention should be defined based on the meaning of the terms and the overall contents of the present invention, not by the simple names of the terms.

When a part "includes" a component throughout the specification, this means that other components may be further included, rather than excluding other components, unless otherwise stated.

Hereinafter, embodiments of the present invention will be described in detail with reference to the accompanying drawings so that those skilled in the art may easily embody the present invention. However, the present invention may be embodied in several different forms and is not limited to the embodiments described herein.

Specific matters including the problems to be solved in the present invention, the means for solving the problems, and the effect of the present invention are included in the embodiments and drawings described below. Advantages and features of the present invention and a method for achieving them will become apparent with reference to the embodiments described below in detail in conjunction with the accompanying drawings.

Hereinafter, the present invention will be described in more detail with reference to the accompanying drawings.

The present invention is characterized in that the amount of data required for learning is minimized, and artificial intelligence is trained and read in a manner as similar as possible to the training of an ophthalmologist who acquire medical knowledge. The present invention is a new architecture in which the structure is designed to be optimized for ophthalmic image reading using the HydraNet (application number 10-2018-0133415) technique, for which a patent has been applied.

When an ophthalmologist reads a fundus image, he or she reads the fundus image in three steps in most cases. That is, first, the ophthalmologist looks at the overall appearance of a picture and infers an approximate category of a disease. Then, secondly, the ophthalmologist closely looks at characteristic lesions in medical textbooks to confirm a specific retinal disease. When a lesion is found at this step, the disease is confirmed, and severity of the disease is graded. In the third step, in order to infer glaucomatous changes, the optic disc is read to find the characteristic factors of glaucoma, such as cup-to-disc ratio, disc hemorrhage, RNFL defect, and LDS (lamina dot sign).

This three-step disease inference process is closely related to actual medical environments. That is, the process of inferring the category of a fundus picture is generally charted in the diagnosis name code or assessment item of the medical record. Accordingly, a large number of training datasets may be easily obtained through a chart database. In addition, although fundus pictures of retinal diseases and glaucoma diagnoses are the same, intensively observed parts are different, and doctors' expertise areas are also separated. That is, since retina specialists and glaucoma specialists are physically separated, charting methods, outpatient groups, and precision diagnosis equipment are different from each other. This means that data for learning is likely to be separated from each other between the retina and the glaucoma, and the amount of learning data or the classification method may be different.

In order to implement this process in a similar way using deep learning, a classifier for roughly classifying diseases and two detectors for finding retinal lesions and optic nerve disc lesions are required at the same time. In order to analyze and train one fundus picture, it is designed to fuse common parts of three different architectures, separate different parts as branches, and then apply the architectures to be suitable for the real world of ophthalmology. In addition, in the present invention, the classifier is newly designed to reflect well the complex medical terminology system that should satisfy an overlapping characteristic, a hierarchical characteristic, and exclusiveness at the same time. The core feature of the present invention may be the mixture of 1) a disease category classifier 2) an optic nerve head localizer for detecting the optic disc and the macula, 3) a key lesion finder, and 4) a small-sized lesion finder with the HydraNet.

Figure 2:
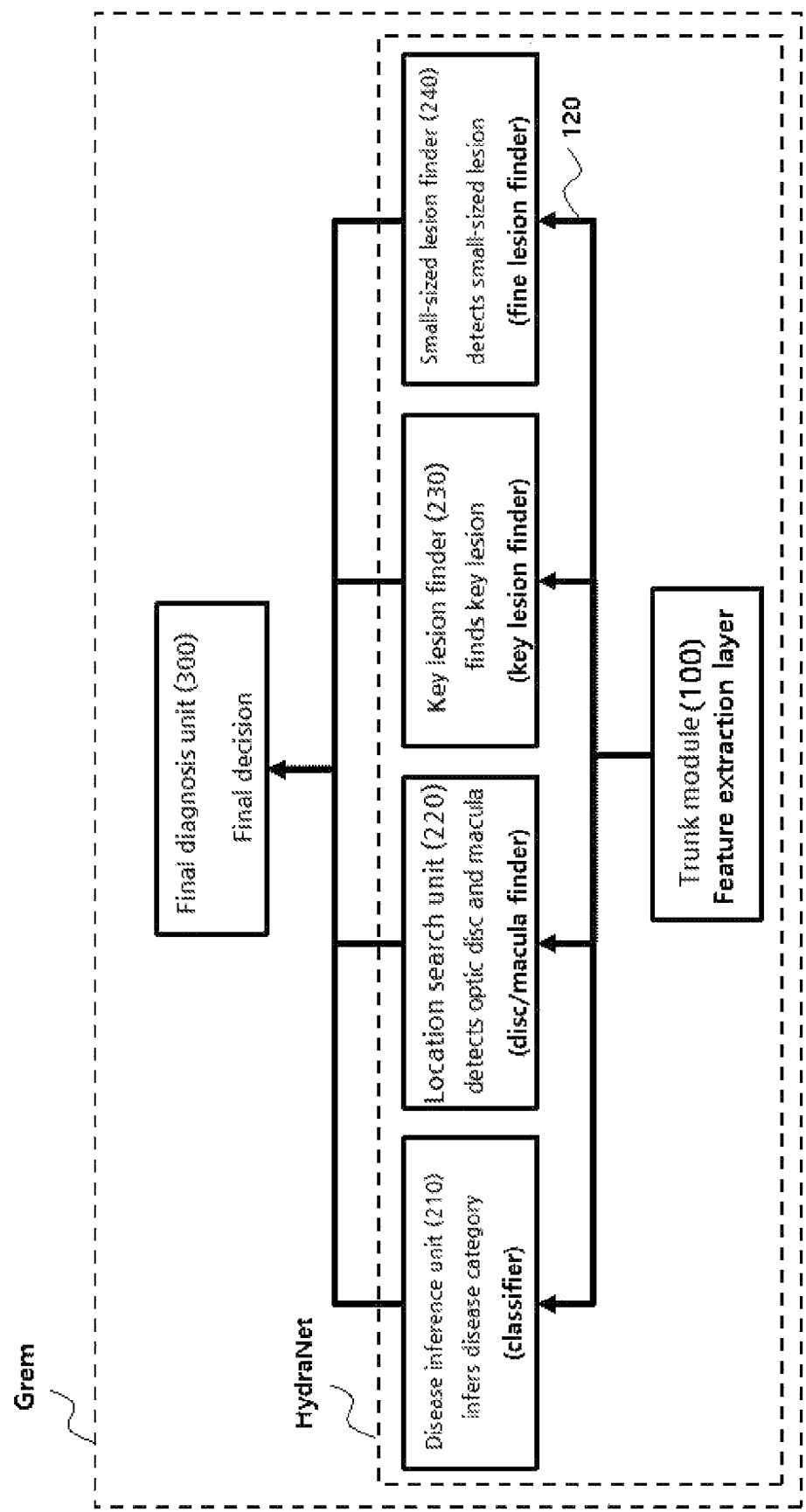
FIG. 2 is a block diagram showing a deep learning architecture system (Glem) for automatic fundus image reading of the present invention.

Accordingly, as shown in FIG. 2, the present invention is largely configured of a trunk module 100, a branch module 200, and a final diagnosis unit 300, and the branch module 200 includes a disease inference unit 210, a location search unit 220, a key lesion finder 230, and a small-sized lesion finder 240. Hereinafter, a deep learning architecture system for automatic fundus image reading of the present invention is named as Grem.

1. Trunk Module (Trunk, 100)

The trunk module 100 is an architecture that combines common parts in a plurality of convolutional neural network (CNN) architectures into one part, in which the CNN architecture has one or more serially arranged feature extraction layer sets respectively configured of a plurality of convolutional layers for performing feature extraction on a fundus image and one pooling layer for performing subsampling to reduce the amount of computation.

The trunk module 100 is a common layer for extracting features of a fundus image using a convolutional neural network (CNN). The trunk module 100 architecture of the present invention increases the input resolution in order to solve the problem that small objects are not detected well. Although it is generally known that accuracy of an artificial neural network is enhanced when the input resolution and the number of convolution layers are increased, when they are increased without limit, it may exceed the memory limit and reduce the calculation speed, and thus a point optimized to some extent is needed.

Accordingly, 640×640 is selected as the input resolution in the present invention, and the reasons are as follows. First, the size of a minimum grid detected by the branch module 200 is 32×32, and second, only one or two small lesions such as microbleed are included in the grid of this size in a fundus image in most cases, and thus this is an appropriate size. In addition, it is confirmed through experiments that the glaucoma detection ability is improved as the resolution of the conventionally used YOLO architecture is increased, and since the glaucoma detection ability is not improved much at a resolution of 640×640 or higher, it is determined that the resolution of 640×640 is optimal for detecting glaucoma.

Table 1 shows a common layer in the trunk module 100 for extracting features of a fundus image using a convolutional neural network (CNN).

TABLE 1

| Layer | Repeat | Filters | Size | Stride | Input | Output |
|---|---|---|---|---|---|---|
| Convolution0 | 1 | 32 | 3 × 3 | 1 | 640 × 640 × 3 | 640 × 640 × 32 |
| Convolution1 | | 64 | 3 × 3 | 2 | 640 × 640 × 32 | 320 × 320 × 64 |
| Convolution2 | | 32 | 1 × 1 | 1 | 320 × 320 × 64 | 320 × 320 × 32 |
| Convolution3 | | 64 | 3 × 3 | 1 | 320 × 320 × 32 | 320 × 320 × 64 |
| Shortcut0 = add (conv2, conv3) | | | | | 320 × 320 × 64 | 320 × 320 × 64 |
| Convolution4 | x4 | 128 | 3 × 3 | 2 | 320 × 320 × 64 | 160 × 160 × 128 |
| Convolution5 | | 64 | 1 × 1 | 1 | 160 × 160 × 128 | 160 × 160 × 64 |
| Convolution6 | | 128 | 3 × 3 | 1 | 160 × 160 × 64 | 160 × 160 × 128 |
| Shortcut1 = add (conv5, conv6) | | | | | 160 × 160 × 128 | 160 × 160 × 128 |
| Convolution7 | x8 | 256 | 3 × 3 | 2 | 160 × 160 × 128 | 80 × 80 × 256 |
| Convolution8 | | 128 | 1 × 1 | 1 | 80 × 80 × 256 | 80 × 80 × 128 |
| Convolution9 | | 256 | 3 × 3 | 1 | 80 × 80 × 128 | 80 × 80 × 256 |
| Shortcut2 = add (conv8, conv9) | | | | | 80 × 80 × 256 | 80 × 80 × 256 |
| Convolution10 | x8 | 512 | 3 × 3 | 2 | 80 × 80 × 256 | 40 × 40 × 512 |
| Convolution11 | | 256 | 1 × 1 | 1 | 40 × 40 × 512 | 40 × 40 × 256 |
| Convolution12 | | 512 | 3 × 3 | 1 | 40 × 40 × 256 | 40 × 40 × 512 |
| Shortcut3 = add (conv11, conv12) | | | | | 40 × 40 × 512 | 40 × 40 × 512 |
| Convolution13 | x4 | 1024 | 3 × 3 | 2 | 40 × 40 × 512 | 20 × 20 × 1024 |
| Convolution14 | | 512 | 1 × 1 | 1 | 20 × 20 × 1024 | 20 × 20 × 512 |
| Convolution15 | | 1024 | 3 × 3 | 1 | 20 × 20 × 512 | 20 × 20 × 1024 |
| Shortcut4 = add (conv14, conv15) | | | | | 20 × 20 × 1024 | 20 × 20 × 1024 |

In addition, a section 110 is an architecture that connects any one branch module 200 among a plurality of branch modules 200 to the trunk module 100. One branch module 200 and the trunk module 100 are combined to form one section 110 for each disease, and since it is configured to calculate using only a corresponding section 110 among a plurality of sections 110 when a new function is used, the required amount of calculation and storage may be decreased at the same time.

Next, a root layer 120 connects the trunk module 100 and the branch module 200 by transferring an output of a specific layer of the trunk module 100 to the branch module 200. The Grem architecture of the present invention is configured of the trunk module 100 in which one or more feature extraction layer sets configured of a plurality of convolutional layers and a pooling layer are arranged in series, the branch module 200 for receiving the output of the trunk module 100 and diagnosing a disease name, and the root layer 120 connecting the trunk module 100 and the branch module 200.

2. Branch Module (200)

The branch module 200 is provided in plurality to receive an output of the trunk module 100 that has generated an architecture for each of the branch modules 200, identify a lesion from a fundus image, and diagnose a corresponding disease name.

As shown in FIG. 2, the branch module 200 is configured of a disease inference unit 210, a location search unit 220, a key lesion finder 230, and a small-sized lesion finder 240.

The disease inference unit 210 infers a disease category by generating a learning data using a matched disease name or disease code in the doctor's charting process.

The location search unit 220 finds the optic nerve head (ONH) from the fundus image, classifies a blind spot ratio (vertical cup-to-disc ratio, VCDR) corresponding thereto, and searches for locations of the optic nerve disc and the macula.

The key lesion finder 230 finds a key lesion that is a component constituting a disease.

The small-sized lesion finder 240 detects small-sized lesions having a size smaller than 10×10 pixels from the fundus image.

2-1. Disease Inference Unit (210)

The disease inference unit 210 performs a function of inferring a disease category by looking at the entire picture. This is similar to an impression acquisition process of a human doctor obtaining a first impression by looking at a picture. The disease inference unit 210 corresponds to a category classifier for classifying a category by looking at the entire fundus image, and does not search for the location of a specific lesion.

Since the learning data of the disease inference unit 210 may be matched 1:1 with a disease name or a disease code in the doctor's charting process, a large amount of data may be obtained w9th ease from previously charted data. This means that there is a significant saving effect in building learning data, which requires considerable effort and cost in the development process of artificial intelligence. The architecture of the disease inference unit 210 is as described below, and becomes a first branch connected to the trunk module 100 described above.

squared error. That is, when the number of disease categories is $N_1$ as shown in [Table 2], the first loss is calculated as follows.

$$loss_{b1} = \sum_{i=1}^{N} (P1_i - T1_i)^2 \qquad \text{[Equation 1]}$$

(Here, $P1_i$ is the probability of a disease to belong to the i-th category through training, which is output as a value between 0 and 1. $T1_i$ is a data value labeled by a human doctor as 1 when it belongs to the disease of the i-th category and as 0 otherwise.)

Figure 3:
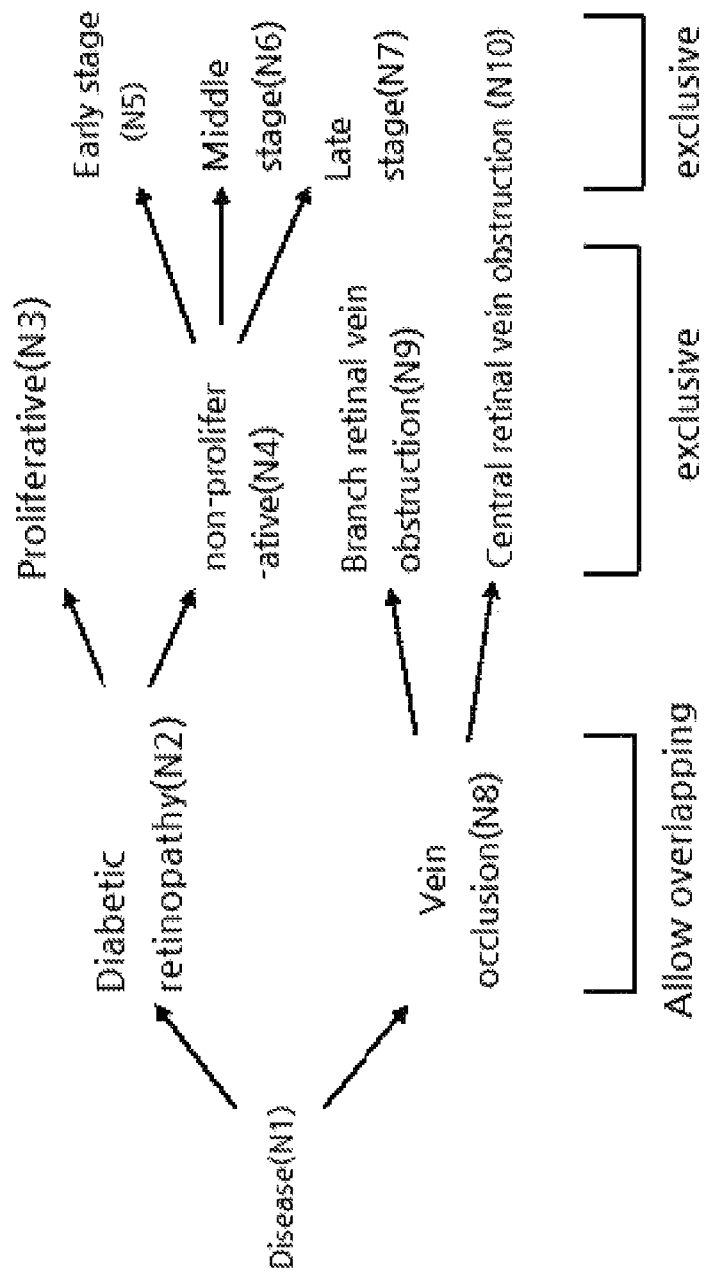
FIG. 3 is a view schematically showing classification of a method reflecting the characteristics of medical terms in a disease inference unit 210.

However, one peculiar thing is that when labeling of a disease by a human doctor is not classified as far as a last child node and ends at a parent node in order to reflect the hierarchical characteristic of medical terms, the value of $T1_i$ is an average of the number of child nodes belonging to the same parent node. For example, when there are 5 child nodes belonging to a specific parent node, $T1_i$ is ⅕=0.2 by dividing 1, which is the value of the parent node, by 5. That is, as a method for reflecting hierarchical labeling during the training of the disease inference unit 210, this is schematically shown in FIG. 3 and will be described below in more detail.

A new result interpretation method reflecting the hierarchical characteristic of medical terms is used to train the disease inference unit 210. Most diseases including eye diseases have a hierarchical structure and are exclusive at a lower level. That is, they have a characteristic of being overlapped at a parent node and exclusive at a child node. Being overlapped means that a person may have several diseases at the same time, and classification of diseases is hierarchical, and sub-classification of a diagnosed disease is exclusive. That is, labeling by learning data of the disease inference unit 210 is performed based on an overlapping characteristic indicating that a person may have several

TABLE 2

| Layer | Filters | Size | Stride | Input | Output |
|---|---|---|---|---|---|
| Convolution0 | 512 | 1 × 1 | 1 | Shortcut4 output | 20 × 20 × 512 |
| Convolution1 | 1024 | 3 × 3 | 1 | 20 × 20 × 512 | 20 × 20 × 1024 |
| Convolution2 | 512 | 1 × 1 | 1 | 20 × 20 × 1024 | 20 × 20 × 512 |
| Convolutions | 1024 | 3 × 3 | 1 | 20 × 20 × 512 | 20 × 20 × 1024 |
| Convolution4 | 512 | 1 × 1 | 1 | 20 × 20 × 1024 | 20 × 20 × 512 |
| Global Average Pooling | | | | 20 × 20 × 512 | 204800 |
| Dense1 | | 256 | | 204800 | 256 |
| Dense2 | | $N_1$ | | 256 | $N_1$ |

(Here, $N_1$ is the number of diseases in the disease inference unit 210).

In [Table 2], the activation function of the last Dense2 layer uses a sigmoid function to independently score a value between 0 and 1 for each disease category. That is, since it is not guaranteed that a person has only one disease, scoring is independently performed using a value between 0 and 1. In addition, as shown in [Table 2], the number of output values is $N_1$ in the Dense2 layer.

In addition, a first loss ($loss_{b1}$) generated when the section 110 connecting the disease inference unit 210 and the trunk module 100 is trained is calculated by [Equation 1]. More specifically, the loss function for training the disease inference unit 210 generally follows a widely used sum of diseases at the same time, a hierarchical characteristic indicating that the category of a disease is hierarchically classified, and exclusiveness indicating that sub-classifications of a diagnosed lesion are mutually exclusive.

For example, diabetic retinopathy and vein occlusion among eye diseases are diseases that may or may not exist simultaneously in one person. That is, they are not mutually exclusive and have an overlapping characteristic. There is a hierarchical characteristic of specifically classifying the vein occlusion into branch retinal vein obstruction and central retinal vein obstruction, further classifying the diabetic retinopathy into proliferative and non-proliferative, and classifying again the non-proliferative into early, middle, and late stages.

As shown in FIG. 3, classifications of diseases may be overlapped at levels of N2 and N8, and may not be overlapped at lower-level classifications. That is, they are mutually exclusive. This is the same for most disease classifications, as well as eye disease classifications. Although disease entities may be overlapped each other, sub-classifications within one disease are not overlapped.

Although the number of outputs of the disease inference unit 210 of the present invention is equal to the number of final child nodes, interpretation while training the disease inference unit 210 follows a hierarchical structure. That is, in the example of FIG. 3, the number of outputs of the last Dense2 layer of the disease inference unit 210 is 6 of final child nodes (N3, N5, N6, N7, N9, N10) shown in green. In the doctor's charting (ground truth), there are cases in which only parent nodes (N2, N8) are classified according to the degree of confidence in diagnosis, or when it is further certain, there are cases in which even the sub-classifications are completed and diagnose is performed below the level.

As described above, when the parent node is no longer subdivided and labeling of the doctor is finished, a value obtained by dividing 1, which is the value of the parent node, by the number of all child nodes belonging to the parent node is used as $T1_i$ in order to calculate $T1_i$ used during the training. For example, when the final diagnosis on a certain fundus image is N2, the number of green child nodes belonging to the node is 4 including N3, N5, N6, and N7, and therefore, $\frac{1}{4}=0.25$ corresponds to the $T1_i$ value of N3, N5, N6, and N7, and is used for calculation of the first loss ($loss_{b1}$) function.

2-2. Location Search Unit (220)

The location search unit 220 is a layer for finding the optic nerve head (ONH), which is the most distinct structure in a fundus image, classifying a blind spot ratio (vertical cup-to-disc ratio, VCDR) corresponding thereto, and searching for locations of the optic nerve disc and the macula. Based on the location of the optic nerve disc found in this way, classification of left eye or right eye of the fundus image is performed, and possibility of glaucoma is inferred. The location search unit 220 uses a detection layer architecture of YOLO V3 of the prior art.

TABLE 3

| Layer | Filters | Size | Stride | Input | Output | Grid |
|---|---|---|---|---|---|---|
| Convolution0 | 512 | 1 × 1 | 1 | Shortcut4 output | 20 × 20 × 512 | |
| Convolution1 | 1024 | 3 × 3 | 1 | 20 × 20 × 512 | 20 × 20 × 1024 | |
| Convolution2 | 512 | 1 × 1 | 1 | 20 × 20 × 1024 | 20 × 20 × 512 | |
| Convolution3 | 1024 | 3 × 3 | 1 | 20 × 20 × 512 | 20 × 20 × 1024 | |
| Convolution4 | 512 | 1 × 1 | 1 | 20 × 20 × 1024 | 20 × 20 × 512 | |
| Convolution5 | 1024 | 3 × 3 | 1 | 20 × 20 × 512 | 20 × 20 × 1024 | |
| Convolution6 YOLO1 | N | 1 × 1 | 1 | 20 × 20 × 1024 | 20 × 20 × N | 20 × 20 |
| Convolution7 | 256 | 1 × 1 | 1 | Convolution4 | 20 × 20 × 256 | |
| Up sample 2x | | | | 20 × 20 × 256 | 40 × 40 × 256 | |
| Concat0 | | | | 40 × 40 × 256, Shortcut3 | 40 × 40 × 768 | |
| Convolution8 | 256 | 1 × 1 | 1 | 40 × 40 × 768 | 40 × 40 × 256 | |
| Convolution9 | 512 | 3 × 3 | 1 | 40 × 40 × 256 | 40 × 40 × 512 | |
| Convolution10 | 256 | 1 × 1 | 1 | 40 × 40 × 512 | 40 × 40 × 256 | |
| Convolution11 | 512 | 3 × 3 | 1 | 40 × 40 × 256 | 40 × 40 × 512 | |
| Convolution12 | 256 | 1 × 1 | 1 | 40 × 40 × 512 | 40 × 40 × 256 | |
| Convolution13 | 512 | 3 × 3 | 1 | 40 × 40 × 256 | 40 × 40 × 512 | |
| Convolution14 YOLO2 | N | 1 × 1 | 1 | 40 × 40 × 512 | 40 × 40 × N | 40 × 40 |
| Convolution15 | 128 | 1 × 1 | 1 | Convolution12 | 40 × 40 × 128 | |
| Up sample 2x | | | | 40 × 40 × 128 | 80 × 80 × 128 | |
| Concat1 | | | | 80 × 80 × 128, Shortcut2 | 80 × 80 × 384 | |
| Convolution16 | 128 | 1 × 1 | 1 | 80 × 80 × 384 | 80 × 80 × 128 | |
| Convolution17 | 256 | 3 × 3 | 1 | 80 × 80 × 128 | 80 × 80 × 256 | |
| Convolution18 | 128 | 1 × 1 | 1 | 80 × 80 × 256 | 80 × 80 × 128 | |
| Convolution19 | 256 | 3 × 3 | 1 | 80 × 80 × 128 | 80 × 80 × 256 | |
| Convolution20 | 128 | 1 × 1 | 1 | 80 × 80 × 256 | 80 × 80 × 128 | |
| Convolution21 | 256 | 3 × 3 | 1 | 80 × 80 × 128 | 80 × 80 × 256 | |
| Convolution22 YOLO3 | N | 1 × 1 | 1 | 80 × 80 × 256 | 80 × 80 × N | 80 × 80 |

(Here, N is the number of filters in the convolution layer immediately before the YOLO V3 layer, and when the number of labels to be detected is k, N=3×(5+k).)

2-3. Key Lesion Finder (230)

The key lesion finder 230 finds a key lesion, which is a component constituting a disease. In addition, image quality of a picture is additionally evaluated to determine whether the image quality of the input fundus image is readable or not, and when it is determined that the image quality is so poor as to significantly lower the reliability of reading, the result may not be output. That is, the key lesion finder 230 classifies the image quality of a fundus image, outputs a result value of the image quality classification, and does not output the result value of the image quality classification when it is determined that reliability of detection of the key lesion is low as the image quality of the fundus image is low.

The architectural structure of the key lesion finder 230 is as shown below.

TABLE 4

| Layer | Filters | Size | Stride | Input | Output |
|---|---|---|---|---|---|
| Convolution0 | 512 | 1 × 1 | 1 | Shortcut4 output | 20 × 20 × 512 |
| Convolution1 | 1024 | 3 × 3 | 1 | 20 × 20 × 512 | 20 × 20 × 1024 |
| Convolution2 | 512 | 1 × 1 | 1 | 20 × 20 × 1024 | 20 × 20 × 512 |
| Convolution3 | 1024 | 3 × 3 | 1 | 20 × 20 × 512 | 20 × 20 × 1024 |
| Convolution4 | 512 | 1 × 1 | 1 | 20 × 20 × 1024 | 20 × 20 × 512 |
| Global Average Pooling | | | | 20 × 20 × 512 | 204800 |
| Dense1 | | 256 | | 204800 | 256 |
| Dense2 | | $N_2$ | | 256 | $N_2$ |

(Here, $N_2$ is the number of key lesions.)

The key lesion finder 230 classifies quality of a fundus image and detects presence of a key lesion, and the labeling is as shown below.

TABLE 5

| Label name | Descriptions |
|---|---|
| Very good | May read all images, and image quality is very good. |
| Good | May read all images, and most readings are correct. |
| Fair | May read all images, but image quality is fair, and reading may be wrong. |
| Poor | Image quality is poor, and only partial reading is possible. |
| Very poor | Image quality is so poor that image cannot be read at all. |
| Lesion 1 | |
| Lesion 2 | |
| Lesion 3 | |
| . . . | . . . |

A second loss ($loss_{b2}$) generated when the section 110 connecting the key lesion finder 230 and the trunk module 100 is trained is calculated by [Equation 2]. The second loss ($loss_{b2}$) function is configured by combining a quality classification part and a key lesion search part. At this point, a weighted sum of squared error is used as the loss function of the key lesion part. That is, a weight value is applied in calculating a loss according to the level of image quality labeled by human. The weight value is classified into very good/good/normal/poor/very poor=1.0/0.75/0.5/0.25/0, and when the image quality is very poor, the weight value is 0, and the loss value of the key lesion is 0, so that backpropagation does not occur.

$$loss_{b2} = \sum_{i=1}^{5}(q_i - Q_i)^2 + W \times \sum_{i=1}^{N}(P2_i - T2_i)^2 \quad \text{[Equation 2]}$$

(Here, $q_i$ is a scoring value labeled by classifying each image quality output through training into five, and $Q_i$ is a scoring value labeled by a human doctor by classifying an image quality into two, and the scoring value is 1 when the image quality labeled as fair, and the scoring value is 0 otherwise. W is a weight value of each image quality classified into very good/good/normal/poor/very poor=1.0/0.75/0.5/0.25/0, $P2_i$ is a scoring value output through training for each of N key lesions, and $T2_i$ is a scoring value labeled by a human doctor for each key lesion, which is 1 when there is a lesion, and 0 otherwise).

2-4. Small-Sized Lesion Finder (240)

The small-sized lesion finder 240 is a branch designed to separately detect a very small but very important lesion from a fundus image, and largely, it has only two labels of red dot (R) and yellow dot (Y). The output format of the small-sized lesion finder 240 is output in the form of (label name, X coordinate, Y coordinate, confidence level) as many as the number of found lesions.

3. Final Diagnosis Unit (300)

The Glem architecture of the present invention is based on HydraNet having four branch modules 200, and it is a layer that determines and outputs a final diagnosis name by integrating the outputs of the four branch modules 200. This layer uses a random forest (RF) algorithm for each disease name. That is, it is a structure in which there is one RF having existence 1 or non-existence 0 of a disease as an output for each of N diseases. The inputs to the N RFs (see FIG. 4) are all the same and configured as shown below.

① The input value from the disease inference unit 210 is a scoring value for each of $N_1$ disease categories.

② The input value from the location search unit 220 is the blind spot ratio (vertical cup-to-disc ratio, VCDR) value, and when two or more optic nerve discs are detected, a VCDRt value calculated by the following [Equation 3] is used.

$$VCDR_t = \sum_{i=1}^{n} \frac{C_i}{C_1 + C_2 + \ldots + C_t} \times VCDR_i \quad \text{[Equation 3]}$$

(Here, $VCDR_i$ is a detected VCDR value, and $C_i$ is a confidence level value of each detected VCDR, which a value output by a YOLO artificial neural network).

③ The input value from the key lesion finder 230 is as many scoring values as $N_2$, which is the number of key lesions.

④ The input value from the small-sized lesion finder 240 is the sum $C_{sum}$ of confidence levels of all dots found for each of $N_3$ labels output from the small-sized lesion finder 240 and the number $N_c$ of the confidence levels.

For example, when five dots corresponding to the label of red dot (R) are found, $C_{sum}$=C1+C2+C3+C4+C5, and $N_c$ is 5.

Figure 4:
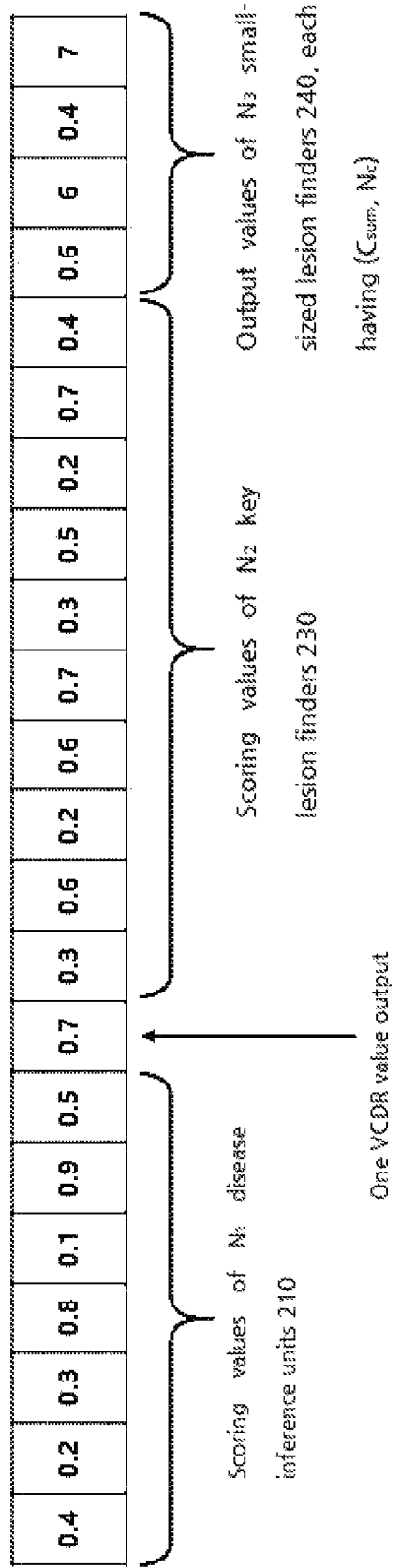
FIG. 4 is a view schematically showing an output value (input value input into the final diagnosis unit 300) output from the branch module 200 as an embodiment implemented by the present invention.

FIG. 4 schematically shows an input vector configured of the four inputs of the four branch modules 200.

Through the means of solving the problems, the present invention may provide an algorithm capable of effectively and automatically reading fundus images by minimizing the amount of data required for learning the fundus images.

In addition, the present invention may provide an algorithm capable of reflecting the classification system of medical terms through mixed classification according to class.

In addition, the present invention may provide a detector finely tuned to fit a lesion of a small size to easily identify a lesion from a fundus image.

In addition, the present invention has an effect of only partially training a system as needed without affecting the entire system while individually training each branch module.

In addition, since common parts are reduced, the present invention may simultaneously decrease the amount of calculation and storage required for computing.

In addition, the present invention may use architectures that perform different functions, such as a classifier branch for classifying the category of fundus images and an object detector branch for finding a specific lesion of interest from a fundus image, as one architecture, while taking advantage of the architectures.

In addition, when there occurs a certain change and the neural network needs to be retrained, the present invention may train only a branch that needs to be retrained, rather than retraining the entire neural network.

In addition, the present invention is efficient in that as only a diagnosis name is separately labeled as needed and only a lesion is labeled as needed when a training set of [image+label] is prepared to train a neural network, labels may be configured separately for each branch.

In addition, the present invention is efficient in that the entire architecture is not used to use a specific function since only a section may be separated to separately use only a function thereof when only an individual function is needed among the functions of the entire neural network.

In addition, the present invention is easy to add a new function since when a new label list and labeled data are prepared after a neural network is already trained, a new function may be created in the neural network by adding only one more branch to process.

In addition, the present invention has an effect of processing fast compared to independently executing individual architectures.

Like this, those skilled in the art will understand that the technical configuration of the present invention described above may be implemented in other specific forms without changing the technical spirit or essential characteristics of the present invention.

Therefore, the embodiments described above should be understood as illustrative and not restrictive in all respects, and the scope of the present invention is indicated by the claims described below rather than the detailed description described above, and the meaning and scope of the claims and all changed or modified forms derived from the equivalent concept thereof should be construed as being included in the scope of the present invention.

The invention claimed is:

1. A deep learning architecture system for automatic fundus image reading, the system comprising:
a trunk module that combines common parts in a plurality of convolutional neural network (CNN) architectures into one part, the CNN architecture having one or more serially arranged feature extraction layer sets respectively configured of a plurality of convolutional layers for performing feature extraction on a fundus image and one pooling layer for performing subsampling to reduce the amount of computation;
a plurality of branch modules for receiving an output of the trunk module that has generated an architecture for each of the branch modules, identifying a lesion from the fundus image, and diagnosing a corresponding disease name;
a section which is an architecture that connects any one branch module among the plurality of branch modules to the trunk module;
a root layer for connecting the trunk module and the branch module by transferring an output of a specific layer of the trunk module to the branch module; and
a final diagnosis unit for integrating diagnosis data received from the plurality of branch modules to determine and output a final disease name, wherein
the branch module includes:
a disease inference unit for inferring a disease category by generating a learning data using a matched disease name or disease code in a doctor's charting process;
a location search unit for finding an optic nerve head (ONH) from the fundus image, classifying a blind spot ratio (vertical cup-to-disc ratio, VCDR) corresponding thereto, and searching for locations of an optic nerve disc and a macula;
a key lesion finder for finding a key lesion that is a component constituting a disease; and
a small-sized lesion finder for detecting a small-sized lesion from the fundus image.

2. The system according to claim 1, wherein a Dense2 layer of the disease inference unit uses a sigmoid function to independently score a value between 0 and 1 for each disease category.

3. The system according to claim 1, wherein a result value of the disease inference unit is equal to the number of final child nodes.

4. The system according to claim 1, wherein a first loss ($loss_{b1}$) generated when the section connecting the disease inference unit and the trunk module is trained is calculated by an equation below:

$$loss_{b1} = \sum_{i=1}^{N} (P1_i - T1_i)^2,$$

wherein $P1_i$ is a probability of a disease to belong to an i-th category through training, which is output as a value between 0 and 1, $T1_i$ is a data value labeled by a human doctor as 1 when it belongs to a disease of the i-th category and as 0 otherwise.

5. The system according to claim 4, wherein in the first loss ($loss_{b1}$), when disease labeling by a human doctor is not classified as far as a last child node and ends at a parent node, a value of T1$_i$ is an average of the number of child nodes belonging to the same parent node.

6. The system according to claim 1, wherein labeling by learning data of the disease inference unit is performed based on an overlapping characteristic indicating that a person may have several diseases at the same time, a hierarchical characteristic indicating that a category of a disease is hierarchically classified, and exclusiveness indicating that sub-classifications of a diagnosed lesion are mutually exclusive.

7. The system according to claim 1, wherein the key lesion finder classifies an image quality of the fundus image, outputs a result value of the image quality classification, and does not output the result value of the image quality classification when it is determined that reliability of detection of the key lesion is low as the image quality of the fundus image is low.

8. The system according to claim 1, wherein a second loss (loss$_{b2}$) generated when the section connecting the key lesion finder and the trunk module is trained is calculated by an equation below:

$$loss_{b2} = \sum_{i=1}^{5}(q_i - Q_i)^2 + W \times \sum_{i=1}^{N}(P2_i - T2_i)^2,$$

wherein, q$_i$ is a scoring value labeled by classifying each image quality output through training into five, Q$_i$ is a scoring value labeled by a human doctor by classifying an image quality into two, the scoring value is 1 when the image quality labeled as fair, the scoring value is 0 otherwise, W is a weight value of each image quality classified into very good/good/normal/poor/very poor=1.0/0.75/0.5/0.25/0, P2$_i$ is a scoring value output through training for each of N key lesions, and T2$_i$ is a scoring value labeled by a human doctor for each key lesion, which is 1 when there is a lesion, and 0 otherwise.

9. The system according to claim 1, wherein the small-sized lesion finder classifies and labels a lesion detected from the fundus image into two lesions, and the lesions are output in the form of (label name, X coordinate, Y coordinate, confidence level) as many as the number of detected lesions.

10. The system according to claim 1, wherein the final diagnosis unit outputs a value indicating existence or non-existence of a disease for N diseases, and input values for the N diseases are values output from the branch module, wherein the input value from the disease inference unit is a scoring value for each of N$_1$ disease categories, the input value from the location search unit is the blind spot ratio (vertical cup-to-disc ratio, VCDR) value, the input value from the key lesion finder is N$_2$ key lesion scoring values, and the input value from the small-sized lesion finder is a sum C$_{sum}$ of confidence levels corresponding to labeling values of the detected lesions and the number N$_c$ of the confidence levels.

11. The system according to claim 10, wherein when the location search unit detects two or more optic nerve discs, a VCDR$_t$ value calculated by an equation below:

$$VCDR_t = \sum_{i=1}^{n} \frac{C_i}{C_1 + C_2 + \ldots + C_t} \times VCDR_i,$$

wherein, VCDR$_i$ is a detected VCDR value, and C$_i$ is a confidence level value of each detected VCDR.

* * * * *